US008335569B2

(12) United States Patent
Aghassian

(10) Patent No.: US 8,335,569 B2
(45) Date of Patent: Dec. 18, 2012

(54) EXTERNAL DEVICE FOR COMMUNICATING WITH AN IMPLANTABLE MEDICAL DEVICE HAVING DATA TELEMETRY AND CHARGING INTEGRATED IN A SINGLE HOUSING

(75) Inventor: Daniel Aghassian, Glendale, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 827 days.

(21) Appl. No.: 12/368,385

(22) Filed: Feb. 10, 2009

(65) Prior Publication Data

US 2010/0204756 A1      Aug. 12, 2010

(51) Int. Cl.
*A61N 1/08*      (2006.01)
(52) U.S. Cl. ............... 607/60; 607/30; 607/31; 607/32; 607/59
(58) Field of Classification Search ............. 607/30–33, 607/59–61
See application file for complete search history.

(56) References Cited

U.S. PATENT DOCUMENTS

| | | | |
|---|---|---|---|
| 5,193,539 A * | 3/1993 | Schulman et al. ............ 607/61 |
| 5,314,457 A | 5/1994 | Jeutter ............ 607/116 |
| 5,769,877 A | 6/1998 | Barreras |
| 5,991,664 A * | 11/1999 | Seligman ............ 607/60 |
| 6,023,641 A | 2/2000 | Thompson |
| 6,073,050 A | 6/2000 | Griffith |
| 6,200,265 B1 | 3/2001 | Walsh et al. |
| 6,248,080 B1 | 6/2001 | Miesel et al. |
| 6,456,883 B1 | 9/2002 | Torgerson et al. |
| 6,505,077 B1 | 1/2003 | Kast ............ 607/61 |
| 6,516,227 B1 | 2/2003 | Meadows ............ 607/46 |
| 6,553,263 B1 | 4/2003 | Meadows ............ 607/61 |
| 6,556,871 B2 | 4/2003 | Schmitt et al. |
| 6,571,128 B2 | 5/2003 | Lebel et al. |
| 6,591,139 B2 * | 7/2003 | Loftin et al. ............ 607/60 |
| 6,658,300 B2 | 12/2003 | Govari ............ 607/60 |
| 6,788,973 B2 | 9/2004 | Davis et al. |
| 6,985,773 B2 | 1/2006 | Von Arx et al. |
| 7,069,086 B2 | 6/2006 | Von Arx |
| 7,072,718 B2 | 7/2006 | Von Arx et al. |
| 7,096,068 B2 | 8/2006 | Mass et al. |

(Continued)

FOREIGN PATENT DOCUMENTS

WO         98/48893         11/1998

(Continued)

OTHER PUBLICATIONS

International Search Report regarding corresponding PCT application No. PCT/US2009/060204, dated Mar. 10, 2010.

(Continued)

*Primary Examiner* — Joseph Stoklosa
(74) *Attorney, Agent, or Firm* — Wong, Cabello, Lutsch, Rutherford & Brucculeri, LLP

(57) ABSTRACT

An improved embodiment of an external device for an implantable medical device system is described herein, where the external device has both circuitry for charging the implantable medical device and circuitry for telemetering data to and from the medical implant contained within a single housing. The external device in one embodiment includes orthogonal radiators in which both the radiators are used for data transfer, and in which at least one of the radiators is used for power transfer. Having charging and data telemetry circuitry fully integrated within a single external device conveniences both patient and clinician.

8 Claims, 5 Drawing Sheets

U.S. PATENT DOCUMENTS

| | | |
|---|---|---|
| 7,177,698 B2 | 2/2007 | Klosterman et al. |
| 7,181,505 B2 | 2/2007 | Haller et al. |
| 7,191,013 B1 * | 3/2007 | Miranda et al. .................. 607/60 |
| 7,200,504 B1 | 4/2007 | Fister .............................. 702/75 |
| 7,226,442 B2 | 6/2007 | Sheppard, Jr. et al. |
| 7,283,867 B2 | 10/2007 | Strother et al. |
| 7,286,880 B2 | 10/2007 | Olson et al. ..................... 607/61 |
| 7,483,743 B2 | 1/2009 | Mann et al. |
| 2002/0038134 A1 | 3/2002 | Greenberg et al. |
| 2004/0098068 A1 | 5/2004 | Carbunaru et al. |
| 2005/0088357 A1 | 4/2005 | Hess et al. |
| 2005/0113887 A1 | 5/2005 | Bauhahn |
| 2005/0143781 A1 | 6/2005 | Carbunaru et al. |
| 2005/0283208 A1 | 12/2005 | Von Arx et al. |
| 2007/0060967 A1 | 3/2007 | Strother et al. |
| 2007/0060980 A1 | 3/2007 | Strother et al. |
| 2007/0233204 A1 | 10/2007 | Lima et al. |
| 2007/0260293 A1 | 11/2007 | Carpenter et al. |
| 2007/0288069 A1 | 12/2007 | Goscha et al. |
| 2008/0046038 A1 | 2/2008 | Hill et al. |
| 2008/0172109 A1 | 7/2008 | Rahman et al. |
| 2008/0183227 A1 | 7/2008 | Sutton |
| 2008/0300654 A1 | 12/2008 | Lambert et al. |
| 2008/0300658 A1 | 12/2008 | Meskens |

FOREIGN PATENT DOCUMENTS

| | | |
|---|---|---|
| WO | 98/48894 | 11/1998 |
| WO | 99/55360 | 11/1999 |
| WO | 2005/032658 A1 | 4/2005 |
| WO | 2005/101660 | 10/2005 |
| WO | 2006/131302 A1 | 12/2006 |
| WO | 2007/047681 A2 | 4/2007 |
| WO | 2007/124325 | 11/2007 |
| WO | 2008/118045 A1 | 10/2008 |

OTHER PUBLICATIONS

U.S. Appl. No. 11/780,369, filed Jul. 19, 2007, Dronov.
U.S. Appl. No. 11/853,624, filed Sep. 11, 2007, Stouffer et al.
U.S. Appl. No. 11/935,111, filed Nov. 5, 2007, Chen et al.
Medtronic, Inc.'s Restore™ Rechargeable Neurostimulation System, as described in Applicant's Information Disclosure Statement filed herewith.
Advanced Neuromodulation Systems (ANS), Inc. Eon™ Neurostimulation Systems IPG, as described in Applicant's Information Disclosure Statement filed herewith.

* cited by examiner

EXTERNAL DEVICE FOR COMMUNICATING WITH AN IMPLANTABLE MEDICAL DEVICE HAVING DATA TELEMETRY AND CHARGING INTEGRATED IN A SINGLE HOUSING

FIELD OF THE INVENTION

The present invention relates to data telemetry and power transfer in an implantable medical device system.

BACKGROUND

Implantable stimulation devices are devices that generate and deliver electrical stimuli to body nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and deep brain stimulators to treat motor and psychological disorders, and other neural stimulators to treat urinary incontinence, sleep apnea, shoulder sublaxation, etc. The present invention may find applicability in all such applications, although the description that follows will generally focus on the use of the invention within a Spinal Cord Stimulation (SCS) system, such as that disclosed in U.S. Pat. No. 6,516,227.

Spinal cord stimulation is a well-accepted clinical method for reducing pain in certain populations of patients. As shown in FIGS. 1A and 1B, a SCS system typically includes an Implantable Pulse Generator (IPG) 100, which includes a biocompatible case 30 formed of titanium for example. The case 30 typically holds the circuitry and power source or battery necessary for the IPG to function, although IPGs can also be powered via external RF energy and without a battery. The IPG 100 is coupled to electrodes 106 via one or more electrode leads (two such leads 102 and 104 are shown), such that the electrodes 106 form an electrode array 110. The electrodes 106 are carried on a flexible body 108, which also houses the individual signal wires 112 and 114 coupled to each electrode. In the illustrated embodiment, there are eight electrodes on lead 102, labeled $E_1$-$E_8$, and eight electrodes on lead 104, labeled $E_9$-$E_{16}$, although the number of leads and electrodes is application specific and therefore can vary.

As shown in FIG. 2, the IPG 100 typically includes an electronic substrate assembly 14 including a printed circuit board (PCB) 16, along with various electronic components 20, such as microprocessors, integrated circuits, and capacitors mounted to the PCB 16. Two radiators are generally present in the IPG 100: a telemetry radiator 13 used to transmit/receive data to/from an external controller 12; and a charging radiator 18 for charging or recharging the IPG's power source or battery 26 using an external charger 50.

As just noted, an external controller 12, such as a hand-held programmer or a clinician's programmer, is used to wirelessly send data to and receive data from the IPG 100. For example, the external controller 12 can send programming data to the IPG 100 to dictate the therapy the IPG 100 will provide to the patient. Also, the external controller 12 can act as a receiver of data from the IPG 100, such as various data reporting on the IPG's status. The external controller 12, like the IPG 100, also contains a PCB 70 on which electronic components 72 are placed to control operation of the external controller 12. A user interface 74 similar to that used for a computer, cell phone, or other hand held electronic device, and including touchable buttons and a display for example, allows a patient or clinician to operate the external controller 12. The communication of data to and from the external controller 12 is enabled by a radiator, which may comprise for example an antenna or (as shown) a radiator 17, which is discussed further below.

The external charger 50, also typically a hand-held device, is used to wirelessly convey power to the IPG 100, which power can be used to recharge the IPG's battery 26. The transfer of power from the external charger 50 is enabled by a radiator which can comprise a radiator 17', which is discussed further below. For the purpose of the basic explanation here, the external charger 50 is depicted as having a similar construction to the external controller 12, but in reality they will differ in accordance with their functionalities as one skilled in the art will appreciate.

Wireless data telemetry and power transfer between the external devices 12 and 50 and the IPG 100 takes place via inductive coupling, and specifically magnetic inductive coupling. To implement such functionality, and as alluded to above, both the IPG 100 and the external devices 12 and 50 have radiators which act together as a pair. In case of the external controller 12, the relevant pair of radiators comprises radiator 17 from the controller and radiator 13 from the IPG. While in case of the external charger 50, the relevant pair of radiators comprises radiator 17' from the external charger and radiator 18 from the IPG.

When data is to be sent from the external controller 12 to the IPG 100 for example, radiator 17 is energized with an alternating current (AC). Such energizing of the radiator 17 to transfer data can occur using a Frequency Shift Keying (FSK) protocol for example, such as disclosed in U.S. patent application Ser. No. 11/780,369, filed Jul. 19, 2007. Energizing the radiator 17 produces an magnetic field, which in turn induces a current in the IPG's radiator 13, which current can then be demodulated to recover the original data.

When power is to be transmitted from the external charger 50 to the IPG 100, radiator 17' is again energized with an alternating current. Such energizing is generally of a constant frequency, and may be of a larger magnitude than that used during the transfer of data, but otherwise the physics involved are similar.

Energy to energize radiators 17 and 17' can come from batteries in the external controller 12 and the external charger 50, respectively, which like the IPG's battery 26 are preferably rechargeable. However, power may also come from plugging the external controller 12 or external charger 50 into a wall outlet plug (not shown), etc.

As is well known, inductive transmission of data or power can occur transcutaneously, i.e., through the patient's tissue 25, making it particularly useful in a medical implantable device system. During the transmission of data or power, the radiators 17 and 13, or 17' and 18, preferably lie in planes that are parallel, along collinear axes, and with the radiators in as close as possible to each other. Such an orientation between the radiators 17 and 13 will generally improve the coupling between them, but deviation from ideal orientations can still result in suitably reliable data or power transfer.

The Inventors consider it unfortunate that the typical implantable medical device system requires two external devices: the external controller 12 and the external charger 50. Both are needed by a typical patient at one time or another with good frequency. The external charger 50 is typically needed to recharge the battery 26 in the IPG 100 on a regular basis, as often as every day depending on the stimulation settings. The external controller 12 can also be needed on a daily basis by the patient to adjust the stimulation therapy as needed at a particular time. Therefore, the patient is encumbered by the need to manipulate two completely independent devices. This means the patient must: learn how to use both devices; carry the bulk of both devices (e.g., when traveling); replace the batteries in both devices and/or recharge them as necessary; pay for both devices, etc. In all, the requirement of two independent external devices is considered inconvenient.

This disclosure provides embodiments of solutions to mitigate these problems.

DETAILED DESCRIPTION

The description that follows relates to use of the invention within a spinal cord stimulation (SCS) system. However, the invention is not so limited. Rather, the invention may be used with any type of implantable medical device system. For example, the present invention may be used as part of a system employing an implantable sensor, an implantable pump, a pacemaker, a defibrillator, a cochlear stimulator, a retinal stimulator, a stimulator configured to produce coordinated limb movement, a cortical and deep brain stimulator, or in any other neural stimulator configured to treat any of a variety of conditions.

An embodiment of an external device for an implantable medical device system is described herein, where the external device has both circuitry for charging the implantable medical device and circuitry for telemetering data to and from the medical implant contained within a single housing. The external device in one embodiment includes orthogonal radiators in which both the radiators are used for data transfer, and in which at least one of the radiators is used for power transfer. Having charging and data telemetry circuitry fully integrated within a single external device conveniences both patient and clinician.

Figure 3:
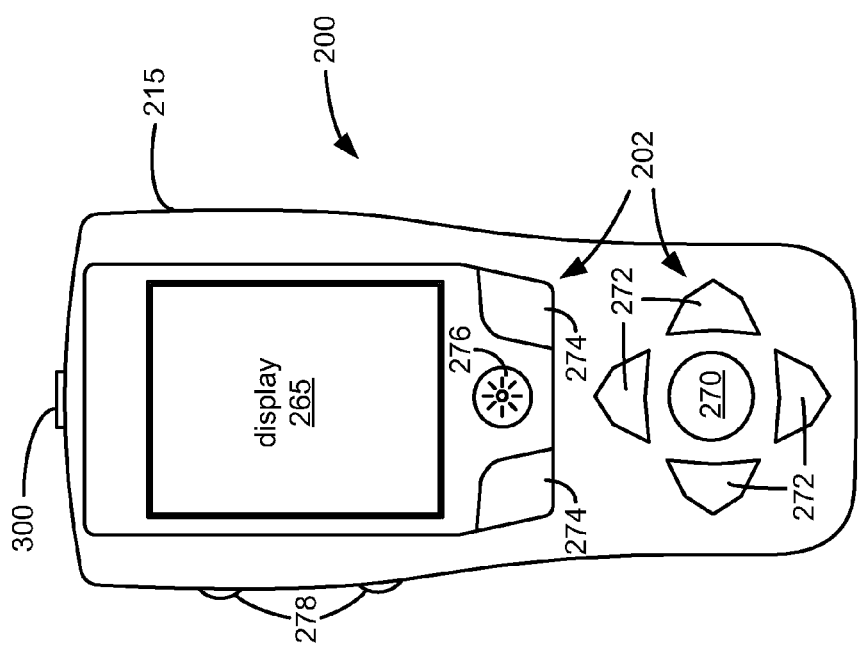
FIG. 3 shows an embodiment of an improved external device containing both data telemetry and charging circuitry within a single housing.

FIG. 3 illustrates one embodiment of a hand-holdable external device 200 that includes both charging and data telemetry circuitry within the same housing 215. As well as housing the charging and data telemetry circuitry, the housing 215 encloses other components, such as a battery, a microcontroller, a printed circuit board, radiator(s), etc., which are explained in detail further below. The shape of the housing, although shown to be substantially rectangular, is not limited to the one shown in FIG. 3. The shape may also be circular, elliptical, etc., and may be designed for easy handling, effective coupling with the IPG 100, etc.

The external device 200 allows the user to control data telemetry and charging functions through a user interface 202. The user interface 202 generally allows the user to telemeter data (such as a new therapy program) from the external device 200 to the IPG 100, to charge the battery in the IPG 100, or to monitor various forms of status feedback from the IPG 100. The user interface 202 may be similar to a cell phone for example, and includes a display 265, an enter or select button 270, and menu navigation buttons 272. Soft keys 278 can be used to select various functions, which functions will vary depending on the status of the menu options available at any given time. A speaker is also included within the housing 215 to provide audio cues to the user (not shown). Alternatively, a vibration motor can provide feedback for users with hearing impairments.

The display 265 optimally displays both text and graphics to convey necessary information to the patient such as menu options, stimulation settings, IPG battery status, external device battery status, or to indicate if stimulation is on or off, or to indicate the status of charging. The display 265 may comprise a monochrome liquid crystal display (LCD) using twisted nematic (TN) or super twisted nematic (STN) liquid crystal technology, as described further in U.S. patent application Ser. No. 11/935,111, filed Nov. 5, 2007, which is incorporated herein by reference in its entirety. The display 265 may also comprise a color display such as a color super twisted nematic (CSTN), a thin-film transistor (TFT) LCD, or an organic light-emitting diode (OLED) display, which again are discussed in the '111 application.

Figures 1A, 1B:
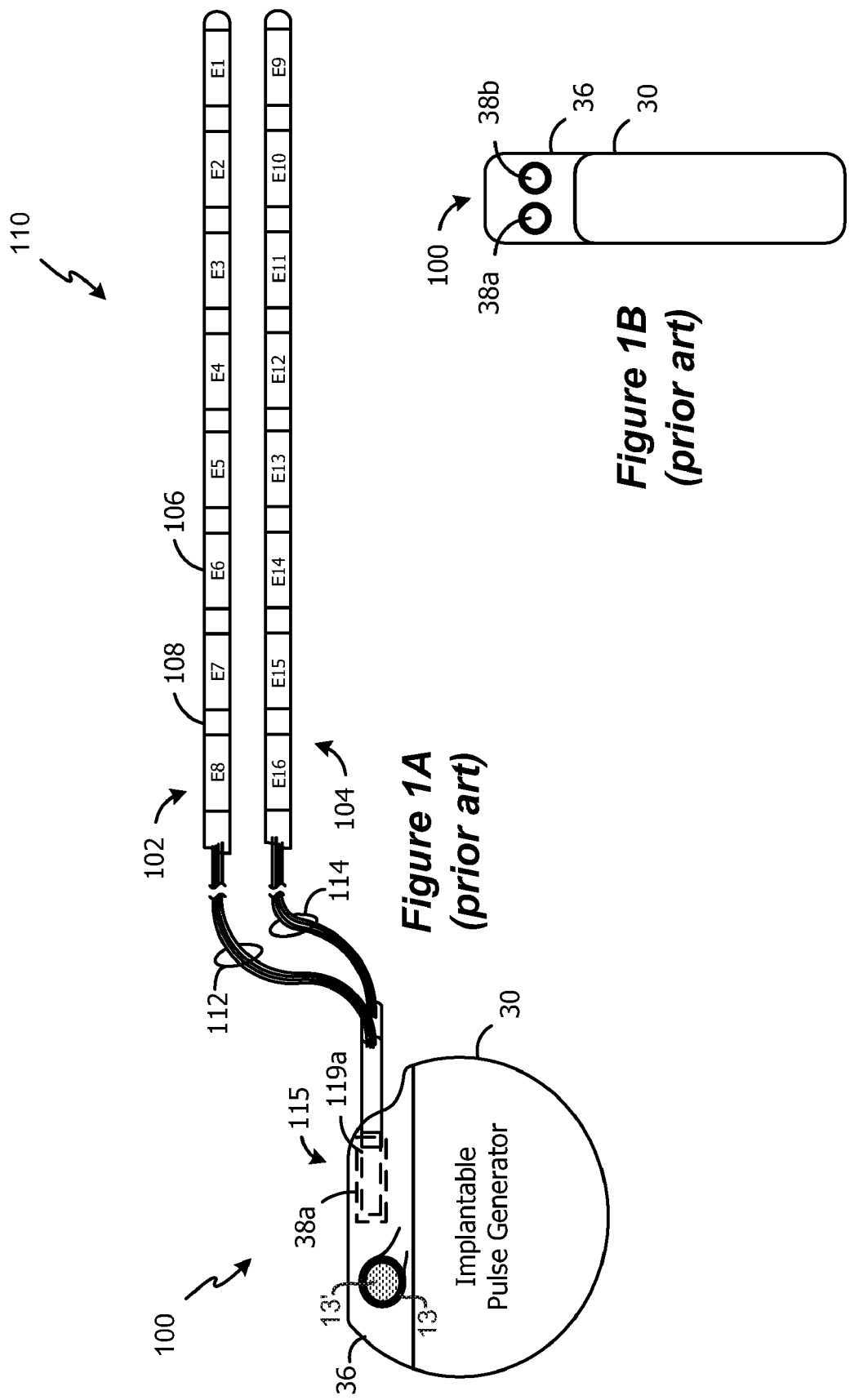
FIGS. 1A and 1B show an implantable pulse generator (IPG), and the manner in which an electrode array is coupled to the IPG in accordance with the prior art.
Figure 2:
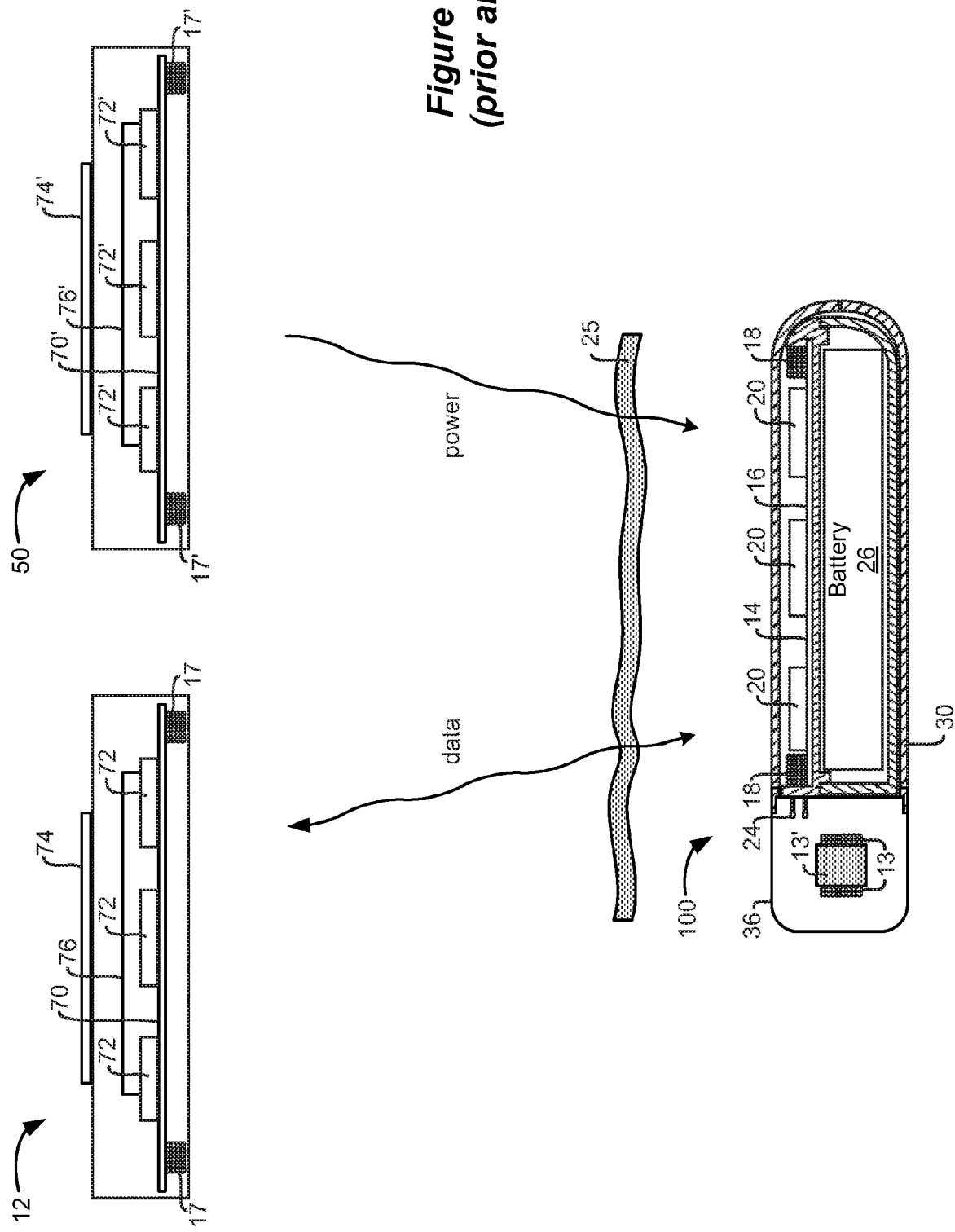
FIG. 2 shows wireless communication of data between an external controller and an IPG, and wireless communication of power from an external charger to the IPG, in accordance with the prior art.
Figure 4:
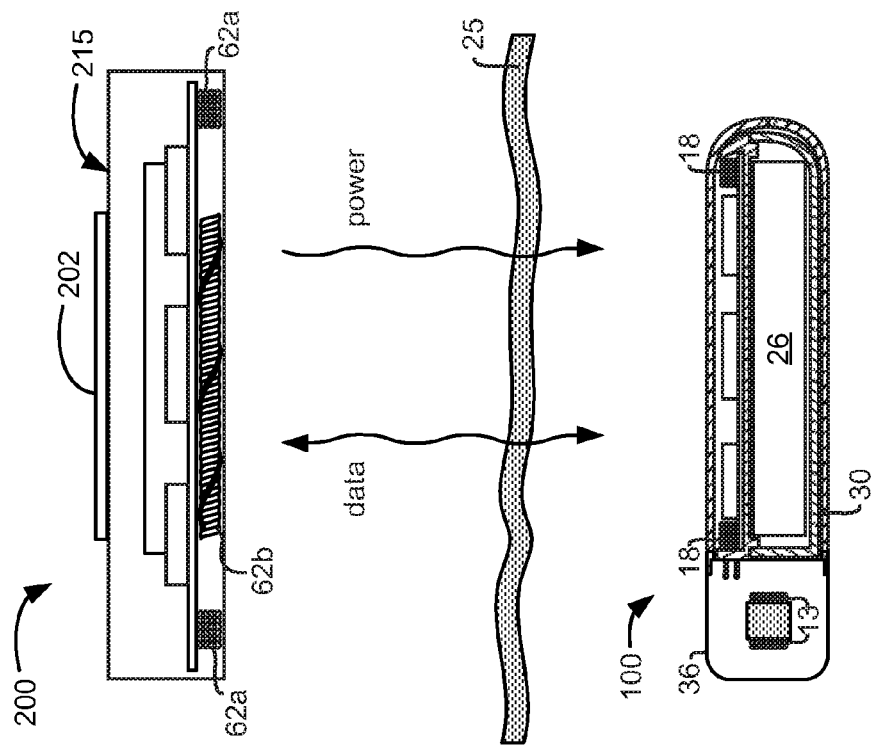
FIG. 4 shows the external device of FIG. 3 communicating both data and power to the IPG.

FIG. 4 illustrates the external device 200 interacting with the IPG 100, and shows both two-way data telemetry and one-way power transfer, both of which occur via magnetic coupling as explained earlier. In one embodiment, two radiators 62a and 62b are provided within the external device, and in one embodiment, both radiators are used for telemetry, while only one is used for charging, as explained further below. In either case, the external device 200 interacts with telemetry coil 13 and charging coil 18 in the IPG 100 in the same manner discussed earlier.

Whether telemetry data or power is transferred to the IPG via radiators 62a and 62b depends upon whether the external device 200 is in telemetry mode or power transfer mode. In telemetry mode, the alternating current energizing radiators 62a and/or 62b can be a carrier signal modulated with the data, e.g., using an FSK modulated protocol as described earlier. In power transfer mode, the radiator 62a can be simply energized with an unmodulated carrier signal. The radiators 62a and 62b can also receive telemetry transmitted by the IPG 100.

Figure 5:
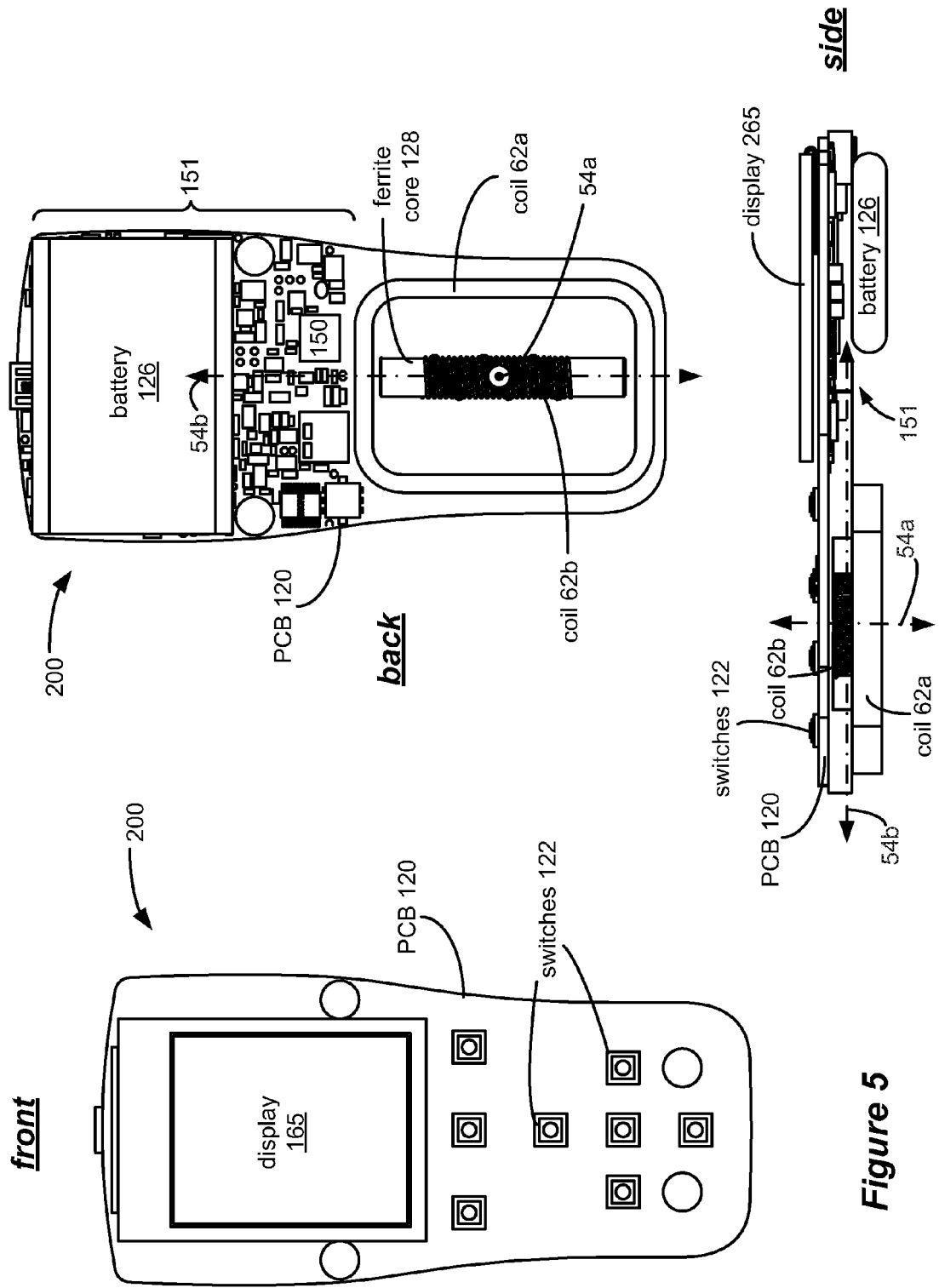
FIG. 5 shows in the internal structure of the external device of FIG. 3.

FIG. 5 shows the internal structure of the external device 200 and the physical orientation of the radiators 62a and 62b as well as some other components. So that the internal components can be more easily seen, the external device 200 is depicted without its outer housing 215, and from front, back, and side perspectives.

The front view discloses a PCB 120 which carries the display 265 and switches 122 comprising user interface 202. Switches 122 couple with the bottom surfaces of soft keys 270-274 shown in FIG. 3 so that when the user presses any of the soft keys 270-274, the corresponding switch is activated to convey the user response to the circuitry on the PCB 120.

The back view shows the circuitry on the underside of PCB 120, including the radiators 62a and 62b and the battery 126. Also visible in part are other integrated and discrete components 151 necessary to implement the charging and data transfer functionality of the external device, such as microcontroller 150.

As seen in the back and side views, the two radiators 62a and 62b are respectively wrapped around axes 54a and 54b which are orthogonal. More specifically, radiator 62b is wrapped in a racetrack, planar configuration around the back of the PCB 120, while radiator 62a is wrapped around a ferrite core 128 and affixed to the PCB 120 by epoxy. Axis 54a is perpendicular to the plane of the radiator 62a (seen more clearly in the side view), while axis 54b is parallel to the length of the core on which radiator 62b is wound. To minimize heating, integrated and discrete components 151 and the battery 126 are placed as far as possible from the electromagnetic fields generated by the radiators. For example, note that none of the integrated and discrete components 151 come within the boundary of radiator 62a. Additionally, if necessary for density purposes, components 151 on the PCB 120 can be placed at least partially underneath the battery 126 as shown. However, it will be appreciated by a person of skill in the art that different arrangements for components 151 are possible.

Axes 54a and 54b are preferably orthogonal, i.e., the angle between axes 54a and 54b is preferably 90 degrees. However, this is not strictly necessary, and any non-zero angle can be used as well. That being said, maximal benefit is achieved when this angle approaches 90 degrees, i.e., approximately 90 as close as mechanical tolerances will allow.

In embodiments in which both radiators 62a and 62b are used for data telemetry, these radiators can carry alternating currents that are substantially 90 degrees out of phase with each other, as described in U.S. patent application Ser. No. 11/853,624, filed Sep. 11, 2007, which is incorporated herein by reference in its entirety. This produces a magnetic field which rotates, and reduces nulls in the coupling between the external device 200 and the receiving telemetry radiator 13 within the IPG 100. The dual radiators 62a and 62b can likewise be used to receive telemetry from the IPG 100.

Figure 6:
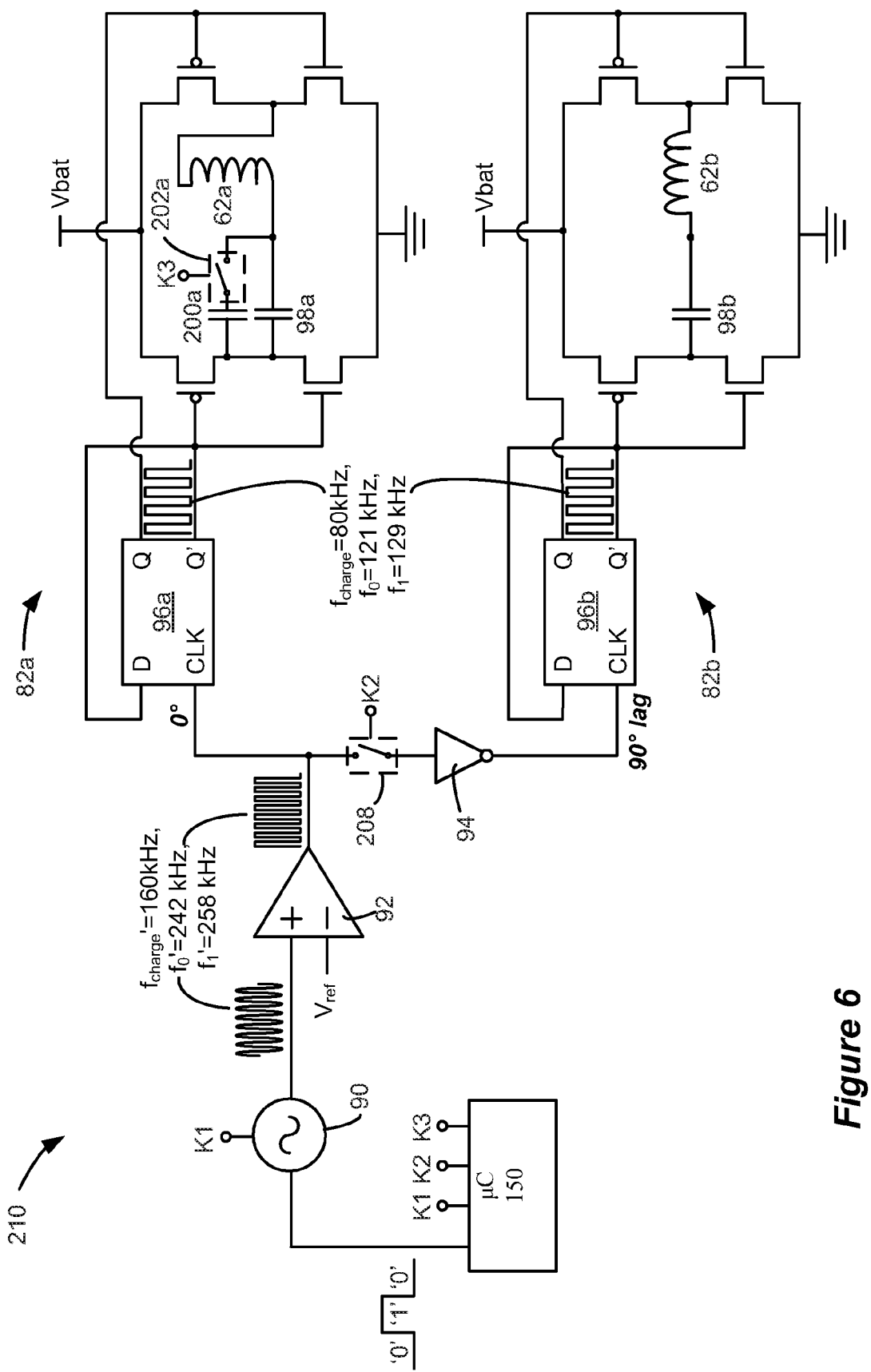
FIG. 6 shows the driving circuitry used to drive the radiator (s) in the external device of FIG. 3.

FIG. 6 depicts driver circuitry 210 used to drive the two radiators 62a and 62b to telemeter data and power to the IPG 100. Operation of the driver circuitry 210 relevant to the transfer of data is discussed first.

Generation of the drive signals for 83a and 83b the two radiators 62a and 62b starts with the external device's microcontroller 150, preferably Part No. MSP430 manufactured by Texas Instruments, Inc., which outputs a string of digital data bits that are ultimately to be wirelessly broadcast to the IPG. These bits are sent to frequency modulation circuitry (modulator) 90 where they are modulated onto a carrier signal. The modulator 90 can comprise a Direct Digital Synthesizer such as part number AD9834 manufactured by Analog Devices, Inc. The carrier signal provided by the modulator 90 can comprise nominally either 250 kHz in the event of data telemetry, or 160 kHz in the event of charging, and is selected by signal K1 as output from the microcontroller 150. Signal K1 can be a single binary signal which for example could control the modulator 90 to produce the frequency suitable for data telemetry (e.g., K1='1') or charging (e.g., K1='0'). Alternatively, K1 could comprise more complex multi-signal bus structures.

In the event of data telemetry, the digital data bits modulate the carrier around its center frequency of $f_c$=250 kHz, such that a logic '0' produces a frequency, $f_0$'=242 kHz, and a logic '1' produces a frequency, $f_1$'=258 kHz. This AC output from the modulator 90 is then turned into a square wave of the same frequency by a comparator or limiter 92 as one skilled in the art will appreciate. As will be seen, later in the driver circuitry 210 these frequencies will be halved to their actual broadcasted values.

During data telemetry, output K2 of the microcontroller 150 closes switch 208, which allows the modulated data to flow to both driver leg 82a which drives radiator 62a, and driver leg 82b which drives radiator 62b. Each leg receives the square wave output from limiter 92 at a clocking input (CLK) of D flip flops 96a and 96b, although the data received at the leg 82b is inverted by an inverter 94. The inverter essentially works a 180 degree shift in the square wave data signal. The complimentary output Q' of each flip flop 96a and 96b is coupled to the corresponding input D. Given this arrangement, and appreciating that the flip flops 96a and 96b can only change data states upon a rising edge of its clock input, the effect is that the outputs (Q/Q') of the flip flops 96a and 96b, i.e., the drive signals 83a and 83b, comprise a square wave signal at half the frequency (i.e., frequencies of $f_0$=121 kHz and $f_1$=129 kHz), but in which the drive signal 83b lags the drive signal 83a by 90 degrees. This approximately 90 degree shift in the lower frequency ($f_c$=125 kHz) signal stems from the approximately 180 degree shift imparted by the inverter 94 at the higher frequency ($f_c$'=250 kHz) signal.

The drive signals 83a and 83b are in turn used to resonate the radiators 62a and 62b, again, with drive signal 83b arriving at radiator 62b with a 90 degree lag. (This phase difference need not be exactly 90 degrees). Resonance is achieved for each radiator 62a and 62b through a serial connection to a tuning capacitor 98a or 98b, respectively, which results in resonant LC circuits, or "tank" circuits. In data telemetry mode, output K3 from the microcontroller 150 is used to open switch 202a, which removes additional capacitor 200a from the tank circuit in leg 82a, thus tuning that tank circuit to resonate roughly at 125 kHz, i.e., suitable for telemetry of the 121 kHz and 129 kHz signals. As one skilled in the art will appreciate, the N-channel (NCH) and P-channel (PCH) transistors are gated by the drive signals 83a and 83b to apply the voltage, Vbat, needed to energize the radiators 62a and 62b. Such voltage Vbat comes from the battery 126 within the external device 200 (FIG. 5). One skilled in the art will appreciate that the disclosed arrangement reverses the polarity of this battery voltage Vbat across the tank circuit (+Vbat followed by −Vbat followed by +Vbat, etc.), which in turn causes the radiators to resonate and therefore broadcast at the frequencies of interest ($f_0$=125 kHz; $f_1$=129 kHz). As noted earlier, such broadcast is received at telemetry radiator 13 in the IPG 100 (FIG. 4).

If two radiators 62a and 62b are used as the antennas for back telemetry (e.g., status data) received from the IPG 100, the external device 200 would additionally contain receiver circuitry. However, because exemplary receiver circuitry is disclosed in the above-incorporated '624 application, such details are not repeated here.

When the external device 200 operates in a charging mode to produce a magnetic field for charging the battery 26 in the IPG 100, the microcontroller 150 changes the status of control signals K1, K2, and K3 sent to the driving circuitry 210. K1 in this mode now indicates to the modulator 90 to output an unmodulated lower frequency more suitable for charging, i.e., $f_{charge}$'=160 kHz. As with the data telemetry mode, this frequency is eventually halved via operation of the flip flop(s) to $f_{charge}$=80 kHz.

Additionally, when charging, control signals K2 and K3 respectively open and close their associated switches 208 and 202a. Opening switch 208 effectively decouples the lower leg 82b of the driver circuit 210, such that only the upper leg 82a, and its planar radiator 62a (FIG. 5), will be used to produce a charging field. In other words, in this embodiment, radiator 62b is not used during charging. However, it should be noted that this is not strictly necessary, and instead radiator 62b could be energized during charging. In such a case, switch 208 could be closed, and similar to operation during telemetry, the produced charging field would rotate due to the 90-degree phase difference. In any event, at least one drive signal 83a or 83b with frequency $f_{charge}$=80 kHz is presented to at least one of the tank circuits.

To accommodate this lower drive frequency from 125 kHz (data telemetry) to 80 kHz (charging), the resonant frequency of the tank circuit in the upper leg 82a is tuned from 125 kHz to 80 kHz. This occurs via control signal K3, which during charging acts to close switch 202a, thus adding capacitor 200a to the tank circuit so as to lower its resonant frequency. Note that the value of the capacitor 200a is selected such that the parallel combination of the capacitors 200a and 98a, in conjunction with the inductance provided by radiator 62a, result in an LC circuit with a resonating frequency substantially equal to 80 kHz. So tuned, the radiator 62a in the external device 200 produces an unmodulated magnetic charging field of 80 kHz, which is received by the charging coil 18 in the IPG (FIG. 4).

In an alternative embodiment, the frequency used for charging, $f_{charge}$, can be the same as the center frequency used for transmitting data, i.e., $f_c$. In such a case, it would not be necessary to tune the tank circuitry when transitioning between the telemetry and charging modes, and switch 202a and capacitor 200a could be dispensed with.

The strength of the magnetic fields produced by the driving circuitry 210 during telemetry and charging and be made adjustable, and can be different between these two modes. Because the alternating current in the tank circuit(s) will be at maximum levels when the frequency of the drive signal 83a and 83b is equal to the tank circuits' resonant frequency, the frequency of the drive signal can be increased or decrease from this optimal value to decrease the current in the tank, and hence the produced field strength. Such trimming of the drive frequency can occur via signal(s) K1 or other signals used to tune the modulator 90. Such control can also be part of a feedback control loop which may include feedback from the IPG 100 to achieve optimal power and data transfer to the receiver circuits in IPG 100.

Radiators 62a and 62b can be made similarly. Alternatively, the radiators 62a and 62b may differ in their composition based on their predominant mode of operation. For example, in FIG. 6 radiator 62b is used only to transfer data during data telemetry mode, while radiator 62a is used for both power and data transmission. Continuous operation of a radiator carrying AC current can result in undesirable heating of the radiator. Therefore, radiator 62a can be designed with specifications that result in minimizing heating. For example, radiator 62a can be an air core radiator where the winding is made of a low resistance material, e.g., litz-wire. Because radiator 62b is used only intermittently for data transfer, it may not experience excessive heating, and can be made of a ferrite rod core and solid copper conductors instead.

Additional measures to minimize heating of the external device 200 can include minimizing eddy currents. For example, the PCB 120, on which the radiators are mounted, may be designed with ground and power traces instead of ground and power planes so as to reduce eddy currents in the PCB. Removal or minimizing of the components 151 from within the radiator 62a (see FIG. 5) is also helpful in this regard. (In actual practice, some components 151 may need to be placed inside the coil area if there is insufficient room outside this area.) Furthermore, active cooling in the form of fans and closed loop temperature control systems can also be employed in the external device 200.

Although particular embodiments of the present invention have been shown and described, it should be understood that the above discussion is not intended to limit the present invention to these embodiments. It will be obvious to those skilled in the art that various changes and modifications may be made without departing from the spirit and scope of the present invention. Thus, the present invention is intended to cover alternatives, modifications, and equivalents that may fall within the spirit and scope of the present invention as defined by the claims.

What is claimed is:

1. An external device for use with an implantable medical device, comprising:
   a hand-holdable housing comprising a display and user interface for controlling telemetry and charging;
   driver circuitry within the housing for driving at least one radiator within the housing, wherein the driver circuitry is adjustable either to a first frequency range or to a second frequency outside the first frequency range; and
   a first and second radiator, wherein the driver circuitry is configured to drive the first and second radiators in the first frequency range for telemetering data to the implantable medical device, and wherein the driver circuitry is configured to drive only the second radiator at the second frequency for providing power to the implantable medical device.

2. The device of claim 1, wherein the data is telemetered at a first frequency within the first frequency range, and wherein the power is provided at the second frequency.

3. The device of claim 2, wherein the second frequency is lower than the first frequency.

4. The device of claim 2, wherein the first frequency is modulated, but the second frequency is unmodulated.

5. The device of claim 1, wherein the driving circuitry comprises a modulator, wherein the frequency of the modulator is adjustable between the first frequency range and the second frequency.

6. The device of claim 1, wherein the second radiator comprises a resonator circuit with a resonant frequency.

7. The device of claim 6, wherein the resonant frequency of the resonator circuit is adjustable between frequencies in the first frequency range and the second frequency.

8. The device of claim 6, wherein the resonator circuit comprises an LC tank circuit.

* * * * *

UNITED STATES PATENT AND TRADEMARK OFFICE
CERTIFICATE OF CORRECTION

PATENT NO. : 8,335,569 B2  
APPLICATION NO. : 12/368385  
DATED : December 18, 2012  
INVENTOR(S) : Aghassian Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 872 days.

Signed and Sealed this  
Sixteenth Day of December, 2014

Michelle K. Lee  
*Deputy Director of the United States Patent and Trademark Office*